United States Patent [19]

Walker

[11] 4,213,991
[45] Jul. 22, 1980

[54] DERIVATIVES OF SUBSTITUTED N-ALKYL IMIDAZOLES AND COMPOSITIONS AND METHODS CONTAINING THE SAME

[75] Inventor: Keith A. M. Walker, Palo Alto, Calif.

[73] Assignee: Syntex (U.S.A.) Inc., Palo Alto, Calif.

[21] Appl. No.: 910,978

[22] Filed: May 30, 1978

[51] Int. Cl.² .................. A01N 9/22; A61K 31/415; C07D 233/54
[52] U.S. Cl. ................... 424/273 R; 424/168; 548/341
[58] Field of Search .................. 424/273; 548/341

[56] References Cited

U.S. PATENT DOCUMENTS

| | | | |
|---|---|---|---|
| 3,658,813 | 4/1972 | Godefroi et al. | 548/341 |
| 3,796,704 | 3/1974 | Metzger et al. | 548/341 X |
| 3,839,574 | 10/1974 | Godefroi et al. | 548/341 X |
| 3,991,202 | 11/1976 | Janssen et al. | 548/341 X |
| 4,017,631 | 4/1977 | Janssen et al. | 548/341 X |
| 4,036,970 | 7/1977 | Walker et al. | 424/273 R |
| 4,036,973 | 7/1977 | Walker et al. | 548/341 X |
| 4,038,409 | 7/1977 | Walker et al. | 424/273 R |
| 4,039,677 | 8/1977 | Walker et al. | 424/273 R |
| 4,055,652 | 10/1977 | Walker et al. | 424/273 R |

Primary Examiner—Dale R. Ore
Attorney, Agent, or Firm—Alan M. Krubiner; Gerard A. Blaufarb

[57] ABSTRACT

Compounds of the formula

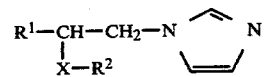

(I)

wherein $R^1$ is phenethyl and $R^2$ is phenyl, each of said phenethyl or phenyl independently being unsubstituted or substituted in the phenyl ring by from 1 to 3 substituents selected from the group consisting of halo, lower alkyl and lower alkoxy with the proviso that at least one of $R^1$ and $R^2$ be substituted by lower alkoxy; X is oxygen or sulfur; and the antimicrobial acid addition salts thereof are useful as antifungal, antibacterial and antiprotozoal agents.

20 Claims, No Drawings

DERIVATIVES OF SUBSTITUTED N-ALKYL IMIDAZOLES AND COMPOSITIONS AND METHODS CONTAINING THE SAME

DETAILED DESCRIPTION OF THE INVENTION

The present invention relates to novel chemical compounds which are derivatives of substituted N-alkyl imidazoles. More particularly, the compounds of the present invention are represented by the formula

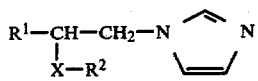

(I)

wherein $R^1$ is phenethyl and $R^2$ is phenyl, each of said phenethyl or phenyl independently being unsubstituted or substituted in the phenyl ring by from 1 to 3 substituents selected from from the group consisting of halo, lower alkyl and lower alkoxy with the proviso that at least one of $R^1$ and $R^2$ be substituted by lower alkoxy; X is oxygen or sulfur; and the antimicrobial acid addition salts thereof.

In a second aspect the present invention is concerned with a method of combatting fungi, bacteria and protozoa by administering a compound of the present invention or a composition containing same.

As used in the specification and the appended claims, unless specified to the contrary, the following terms have the meaning indicated. The term "lower alkyl" refers to a straight or branched chain monovalent substituent consisting solely of carbon and hydrogen, containing no unsaturation, and having from one to four carbon atoms. Examples of lower alkyl groups are methyl, ethyl, n-propyl, isopropyl, n-butyl, isobutyl, and t-butyl. The term "halo" refers to fluoro, chloro and bromo. The term "phenethyl" refers to 2-phenylethyl. "Antimicrobial acid addition salts" of the subject bases refers to those salts which retain the antimicrobial properties of the free bases and which are neither biologically nor otherwise undesirable, formed with, for example, inorganic acids such as hydrochloric acid, hydrobromic acid, sulfuric acid, nitric acid or phosphoric acid; or organic acids such as acetic acid, propionic acid, glycolic acid, lactic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, and the like.

All compounds of formula (I) possess at least one chiral center, i.e., the carbon atom to which are attached the $R^1$, X, $CH_2$ and H moieties. Accordingly, the compounds of the present invention may be prepared in either optically active form, or as a racemic mixture. Unless otherwise specified, the compounds described herein are all in the racemic form. However, the scope of the subject invention herein is not to be considered limited to the racemic form, but to encompass the individual optical isomers of the subject compounds.

If desired, racemic intermediates or final products prepared herein may be resolved into their optical antipodes by conventional resolution means known per se, for example, by the separation (eg., fractional crystallization) of the diastereomeric salts formed by reaction of, e.g., racemic compounds of formula (I) with an optically active acid, or by the separation of the diastereomeric salts or esters formed by reaction of racemic compounds of formula (II), infra, with an optically active acid. Exemplary of such optically active acids are the optically active forms of camphor-10-sulfonic acid, α-bromo-camphor-sulfonic acid, camphoric acid, menthoxy-acetic acid, tartaric acid, malic acid, diacetyl-tartaric acid, pyrrolidone-5-carboxylic acid, and the like. The separated pure diastereomeric salts or esters may then be cleaved by standard means to afford the respective optical isomers of the compounds of formula (I) or (II).

The subject compounds of formula (I) exhibit antifungal, antibacterial and antiprotozoal activity. For example, compounds of the present invention exhibit antifungal activity against human and animal pathogens such as Microsporum audouini,
Microsporum gypseum,
Microsporum canis,
Epidermophyton floccosum,
Trichophyton mentagrophytes,
Tricophyton rubrum
Trichophyton tonsurans
Trichophyton concentricum
Candida albicans, and
Cryptococcus neoformans.

The compounds of the present invention also exhibit antifungal activity against the following fungi primarily of agricultural significance.

Aspergillus flavus, Aspergillus niger, Cladosporium herbarum, Penicillium oxalicum, Fusarium graminearum, Penicillium spinulosum Penicillium notatum, and, Pithomyces chartarum.

In addition, the compounds of the present invention exhibit antibacterial activity against human and animal pathogens, such as Staphylococcus aureus,
Streptococcus faecalis,
Corynebacterium acnes,
Erysipelothrix insidiosa, and
Pasteurella multocida.

Moreover, the compounds of the present invention exhibit anti-protozoal activity against protozoa such as Trichomonas vaginalis and Trichomonas foetus.

In general, the subject compounds of the instant invention exhibit a low level of toxicity and are well tolerated by the host. Moreover, these compounds demonstrate good solubility in the stratum corneum. Since dermatophyte (i.e., parasitic fungal) infections are usually localized in the dead tissue of the stratum corneum, solubility of anti-fungal agents in this tissue significantly enhances their effectiveness.

In view of the aforementioned activities, the subject compounds are found to be useful antimicrobials, having not only pharmaceutical but also agricultural and industrial application.

Accordingly, a further aspect of the present invention relates to compositions for pharmaceutical, agricultural, and industrial use, which compositions comprise the subject compounds of formula (I) in combination with a suitable carrier. A still further aspect of the present invention relates to methods of inhibiting the growth of fungi, bacteria and protozoa by applying to a host object containing, or subject to attack by, fungi, bacteria or protozoa, an effective amount of a compound of the present invention or a suitable composition containing same.

In pharmaceutical applications, compositions may be solid, semi-solid or liquid in form such as tablets, capsules, powders, suppositories, liquid solutions, suspensions, creams, lotions, ointments and the like. Pharmaceutically acceptable non-toxic carriers or excipients normally employed for solid formulations include tricalcium phosphate, calcium carbonate, kaolin, bentonite, talcum, gelatin, lactose, starch and the like; for semisolid formulations there may be mentioned, for example, poly-alkylene glycols, vaseline and other cream bases; for liquid formulations there may be mentioned, for example, water, oils of vegetable origin and low boiling solvents such as isopropanol, hydrogenated naphthalenes and the like. The pharmaceutical compositions containing the compounds of the present invention may be subjected to conventional pharmaceutical expedients such as sterilization and can contain conventional pharmaceutical excipients such as preservatives, stabilizing agents, emulsifying agents, salts for the adjustment of osmotic pressure and buffers. The compositions may also contain other therapeutically active materials. In pharmaceutical applications, the subject compounds and compositions may be administered to humans and animals by conventional methods, e.g., topically, orally, parenterally and the like. Parenteral administration includes intramuscular as well as subcutaneous and intravenous administration. Intravenous injection of imidazole-type anti-fungals has been demonstrated to be effective in the treatment of systemic mycoses (see for example, Drugs, 9, pp. 419-420, 1975, which describes the intravenous administration of miconazole, i.e. 1-[2,4-dichloro-$\beta$-(2',4'-dichlorobenzyloxy)phenethyl]imidazole nitrate, to patients with systemic candidiasis). Topical application is the preferred method of administration for pharmaceutical applications. For such treatment, an area having an existing fungal, bacterial or protozoal growth, or to be protected against attack by fungi, bacteria or protozoa, may be treated with the subject compounds or compositions by, for example, dusting, sprinkling, spraying, rinsing, brushing, dipping, smearing, coating, impregnating and the like. Topical pharmaceutical compositions containing the compounds of the present invention exhibit anti-fungal anti-bacterial and anti-protozoal activity over a wide range of concentration, for example, from about 0.1 to 10.0% by weight of the composition. In any event, the composition to be administered will contain a quantity of the subject compound in an amount effective for relief or prevention of the specific condition being treated.

The pharmaceutical compositions hereof typically comprise one or more subject compounds of Formula (I) and a pharmaceutically acceptable, non-toxic carrier.

In general, for systemic (e.g., oral or parenteral administration it is expedient to administer the active ingredient in amounts between about 1 and 100 mg./kg. body weight per day, preferably between about 5 and 50 mg./kg. body weight per day, preferably distributed over several applications (e.g., in 3 individual doses) in order to achieve most effective results. For localized (e.g. topical) administration, however, proportionately less of the active ingredient is required.

The exact regimen for pharmaceutical administration of the compounds and compositions disclosed herein will necessarily be dependent upon the needs of the individual subject being treated, the type of treatment, e.g., whether preventative or curative, the type of organism involved and, of course, the judgment of the attending practitioner.

In agricultural applications, the subject compounds may be applied directly to plants (e.g., seeds or foilage) or to soil. For example, compounds of the present invention may be applied to seeds alone or in admixture with a powdered solid carrier. Typical powdered carriers are the various mineral silicates, e.g., mica, talc, pyrophyllite, and clays. The subject compounds may also be applied to the seeds in admixture with a conventional surface-active wetting agent with or without additional solid carrier. Surface-active wetting agents that can be used are any of the conventional anionic, non-anionic or cationic types. As a soil treatment for fungi and the like, the subject compounds can be applied as a dust in admixture with sand, soil or a powdered solid carrier such as a mineral silicate with or without additional surface-active agent, or the subject compounds can be applied as an aqueous spray optionally containing a surface-active dispersing agent and a powdered solid carrier. As a foliage treatment, the subject compounds may be applied to growing plants as an aqueous spray which contains a surface-active dispersing agent with or without a powdered solid carrier and hydrocarbon solvents.

In industrial applications, the subject compounds may be used to control bacteria and fungi by contacting the pathogens with the compounds in any known manner. Materials capable of supporting bacteria and fungi may be protected by contacting, mixing or impregnating these materials with the subject compounds. In order to increase their effect, the subject compounds may be combined with other pesticidal control agents such as fungicides, bactericides, insecticides, miticides and the like. A particularly important industrial/agricultural use for the subject compounds of the present invention is as a food preservative against bacteria and fungi which cause deterioration and spoilage of foods.

The compounds of formula (I) may be considered to consist of two subclasses, those of formulas (Ia) and (Ib) shown below

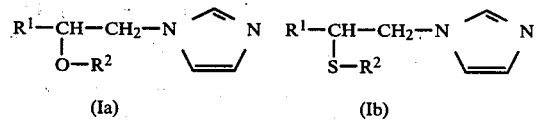

(Ia)  (Ib)

wherein $R^1$ and $R^2$ are as defined above.

Both groups of compounds may be prepared from common intermediates having a free hydroxyl group which is then converted to the ether or thioether, as the case may be, and which may be prepared by a variety of methods.

One preferred subclass of compounds of formula I are those wherein $R^1$ has a 4-halo or 4-lower alkyl substituent and $R^2$ has a lower alkoxy substituent.

Particularly preferred compounds within this subgenus are those wherein $R^1$ has a 4-chloro or 4-methyl substituent and $R^2$ has a lower alkoxy substituent in the 2-position. The 2-substituent is preferably methoxy when $R^2$ is monosubstituted.

Another preferred subgenus of compounds of formula I are those wherein $R^1$ has a 4-alkoxy substituent and $R^2$ has a 2-halo, 2-lower alkyl or 2-lower alkoxy substituent.

Particularly preferred compounds within this subgenus are those wherein $R^1$ has a 4-methoxy substituent and $R^2$ has a 2-chloro, 2-methyl or 2-methoxy substituent.

For both of the above subgenuses, compounds wherein X is sulfur are particularly preferred.

As mentioned above, compounds of Formula (I) may be prepared by forming an ether or thioether from a suitable alcohol of formula (II)

(II)

wherein $R^1$ is as defined above. Compounds of formula (II) may be prepared by a variety of reaction sequences.

Certain compounds of formula (II) may be prepared according to reaction scheme A shown below.

Reaction Scheme A

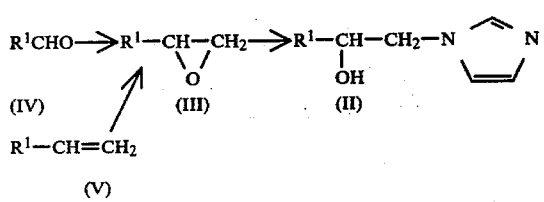

In this reaction scheme the imidazole alcohol of formula (II) is formed by opening of a terminal epoxide of formula (III) with imidazole. This reaction is generally carried out using at least one mole and preferably an excess of imidazole relative to epoxide. The reaction may either be carried out in the absence of solvent or, preferably, in an inert organic solvent, for example, a solvent such as tetrahydrofuran, dimethylformamide, hexamethylphosphoramide, acetonitrile, and the like. The epoxide opening is preferably carried out using a metal salt (preferably an alkali metal salt) of imidazole, e.g., sodium imidazole, preferably catalytically in the presence of imidazole free base as proton source. A preferred solvent is tetrahydrofuran. The temperature normally employed for such epoxide opening is in the range of from about 0° to about 100° C. most preferably from about 20° to about 85° C.

Epoxides of formula (III), insofar as they may not be known or readily available, may be prepared by a variety of well known methods, for example epoxidation of a terminal olefin (e.g., (V)) with, for example, a peracid, or by reaction of an aldehyde having one fewer carbon atoms (e.g., (IV)) with the ylide prepared from trimethylsulfoxonium iodide or trimethylsulfonium iodide as described, for example, in J. Am. Chem. Soc., 84, p. 867 (1962); ibid, 87, p. 1353 (1965).

Another reaction scheme for preparing certain compounds of formula (II) is shown in reaction scheme B presented below Reaction Scheme B

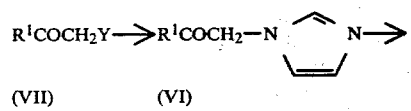

(VII)         (VI)

-continued
Reaction Scheme B

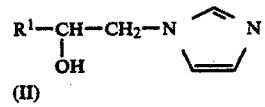
(II)

wherein Y is chloro or bromo.

In this reaction scheme the hydroxy compound of formula (II) is prepared by reduction of the corresponding ketone (VI), which in turn is prepared by reaction of an α-halo ketone (VII) with imidazole.

The α-halo ketones may be readily prepared by, for example, conversion of the acyl chloride $R^1COCl$ to the diazo ketone $R^1COCHN_2$ diazomethane, followed by treatment with acid HY or as described in Reaction Scheme C, infra (see Compound X).

The α-halo ketone is contacted with imidazole in an inert organic solvent to afford the keto imidazole of formula (VI). The reaction is carried out utilizing at least a molar amount and, preferably, an excess of imidazole relative to halo ketone. The reaction may be carried out in the absence of solvent or, preferably, in an inert organic solvent such as for example dimethylformamide, hexamethylphosphoramide, acetonitrile, and the like. The reaction is suitably carried out at a temperature initially between about −10° and 100° C. most preferably between about 0° and 25° C.

In the next step the keto imidazole of formula (VI) is reduced to the hydroxy imidazole of formula (II) utilizing a conventional metal hydride reducing agent such as, for example, sodium borohydride. The reaction is suitably carried out in an alcoholic solvent such as, for example, methanol or ethanol at a reduced temperature, for example, between about −10° and +25° C., most preferably about 0° C.

Certain compounds of formula (II) may be prepared according to a further reaction sequence. This is illustrated below in reaction scheme C.

Reaction Scheme C

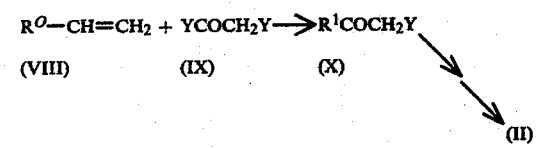

wherein $R^1$ is $R^OCH_2CH_2$ and Y is chloro or bromo.

In this scheme the ω-halo ketone of formula (X) is prepared starting with a terminal olefin of formula (VIII) and an ω-halo acetyl halide of formula (IX). This reaction is carried out under the conditions described in G. Olah, "Friedel Crafts and Related Reactions", Vol. 3, Part 2, Interscience Publishers, New York (1964).

A preferred method for preparing compounds of formula (II) is illustrated in reaction scheme D, shown below Reaction Scheme D

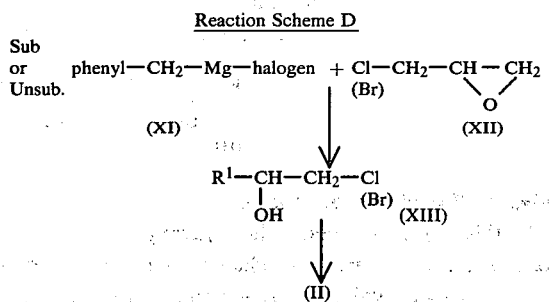

In this scheme the appropriately substituted benzyl Grignard reagent (XI) (preferably the benzyl magnesium chloride) is reacted with epichorohydrin (or epibromohydrin) (XII) to afford the halohydrin (XIII). This reaction is carried out in typical solvents for performing Grignard reactions, namely ether containing solvents, preferably diethyl ether, and at temperatures between about 20° and 50° C.

The halohydrin (XIII) is then converted to the imidazole alcohol (II) by treatment with an alkali metal (preferably sodium) salt of imidazole in a polar aprotic solvent such as dimethylformamide at a temperature between about 50° and 100° C.

Alternatively, treatment of halohydrin with base will afford the epoxide (III) described above.

Compounds of formula (I) may be prepared from the compounds of formula (II) by a two-step sequence involving conversion of the hydroxy group to a suitable leaving group such as a halide (e.g., a chloride or bromide) or a sulfonate ester (e.g., methanesulfonate or p-toluenesulfonate) which is then reacted with the corresponding phenol $R^2OH$ or thiophenol $R^2SH$, optionally in the presence of base, or with a metal salt (preferably an alkali metal salt such as the sodium or potassium salt) of the phenol or thiophenol.

The conversion from the alcohol to the halide or sulfonate ester is carried out by means well known in the art. For example, the alcohol may be halogenated using a halogenating agent such as thionyl chloride or thionyl bromide, either neat, or in an inert organic solvent such as dichloromethane or chloroform, at a temperature between about 0° and 80° C., preferably between about 20° and 80° C. The halogenation reaction may be carried out in the presence of a molar equivalent of a base (e.g. pyridine) if desired. Alternate halogenation procedures include, for example, the use of triphenylphosphine with either carbon tetrachloride, carbon tetrabromide, or N-chloro (or N-bromo) succinimide. When utilizing thionyl chloride or thionyl bromide without the use of added base, the hydrochloride or hydrobromide salt of the corresponding halo compound is produced. This salt may be neutralized (e.g., with potassium carbonate) prior to its use in the alkylation step, or the salt may be used directly if excess phenol or thiophenol salt is utilized.

Sulfonate esters may be prepared by the standard procedure of treating the alcohol with an excess of, for example, methanesulfonyl chloride or p-toluenesulfonyl chloride, in the presence of a base, for example, pyridine or triethylamine. This rection is carried out at a temperature from about −20° to +50° C., preferably between about 0° and 20° C.

The halide or sulfonate ester prepared as described above, is then treated with the corresponding phenol or thiophenol, optionally in the presence of base, or with a metal salt (preferably an alkali metal salt such as the sodium or potassium salt) of the phenol or thiophenol, in the presence of an inert organic solvent such as acetone, methanol, and the like, at a temperature of about 20° to about 80° C.

In a preferred reaction compounds of formula (I) wherein X is oxygen may be directly prepared from compounds of formula (II) in one step by reaction with the coresponding phenol in the presence of a triarylphosphine (preferably triphenylphosphine) and a dialkyl azodicarboxylate (preferably dimethyl or diethyl azodicarboxylate). This rection is preferably carried out in an inert solvent such as an ether (preferably tetrahydrofuran or diethyl ether) a hydrocarbon (preferably benzene or toluene) or dimethylformamide at a temperature between about 0° and 40° C.

Compounds of Formula (I) wherein X is sulfur may also be prepared as depicted in Reaction Scheme E below.

Reaction Scheme E

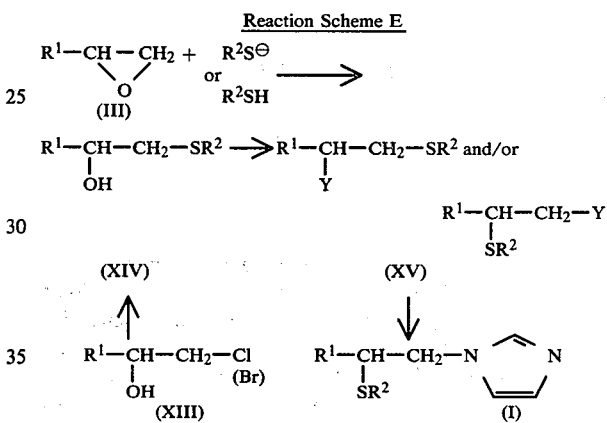

wherein Y is a leaving group.

In this scheme the epoxide of formula (III) described earlier, is opened with a thiophenol or a metal salt thereof, to afford the compound of formula (XIV). This reaction is carried out utilizing, preferably, an alkali metal salt of the thiophenol, most preferably the sodium or potassium salt, in an inert organic solvent such as, for example, tetrahydrofuran or acetone at a temperature of between about 0° and 67° C., or using excess free thiophenol in the presence of an acid catalyst, e.g., perchloric acid, or $BF_3$ in an inert solvent such as dichloromethane or nitromethane, or in the absence of added solvent.

In the next step the hydroxy group of the compound of formula (XIV) is converted to a leaving group such as a halide (e.g., chloro or bromo) or sulfonate ester (e.g., p-toluenesulfonate or methanesulfonate) by treatment with, e.g., a halogenating agent such as, for example, thionyl chloride, neat, or preferably in an inert solvent such as dichloromethane, or with, for example, p-toluenesulfonyl chloride, in a solvent such as tetrahydrofuran, dichloromethane, and the like. The product of formula (XV) may exist in either or both forms depicted, and may be interconvertible through or isolable as an episulfonium salt.

In the final step, the compound of formula (XV) is converted to the final product of formula (I) by treatment with imidazole. This reaction is carried out in an inert organic solvent such as for example acetonitrile, dimethylformamide, and the like, at a temperature of about 0° to about 80° C.

The subject compounds of the instant invention can be isolated as free bases; however, since many of the compounds in base form are oils, it is more convenient to isolate and characterize the compounds as acid addition salts. These salts are prepared in the usual manner, i.e., by reaction of the base compound with a suitable inorganic or organic acid, described above. Salts formed with dibasic acids (e.g., oxalic acid) may generally contain one or two molecules of base per molecule of acid. All oxalates described herein contain one molecule of oxalic acid per molecule of imidazole base. If desired, the salts can be readily converted to the free base form by treatment with alkali, such as potassium carbonate, sodium carbonate or sodium or potassium hydroxide.

In summary, then, this aspect of the present invention relates to a process for the preparation of a compound of the formula

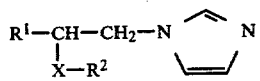

(I)

wherein $R^1$ is phenethyl and $R^2$ is phenyl, each of said phenethyl or phenyl independently being unsubstituted or substituted in the benzene ring by from 1 to 3 substituents selected from the group consisting of halo, lower alkyl and lower alkoxy, with the proviso that at least one of $R^1$ and $R^2$ be substituted by lower alkoxy; and the antimicrobial acid addition salts thereof which comprises:

a. converting a compound of the formula

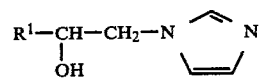

(II)

wherein $R^1$ is as above to an ether by reaction with $R^2OH$ wherein $R^2$ is as above and a dialkyl azodicarboxylate and a triaryl phosphine or b. converting a compound of the formula

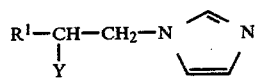

wherein $R^1$ is as defined above and Y is a leaving group, or an acid addition salt thereof, to an ether or thioether by reaction $R^2OH$, $R^2XH$, or a salt thereof, wherein $R^2$ is as above, or c. reacting a compound of the formula

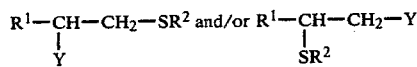

or an episulfonium salt thereof wherein $R^1$, $R^2$ and Y are as above, with imidazole, and d. optionally converting a free base to its acid addition salt, or e. optionally converting an acid addition salt to the corresponding free base.

The following specific examples are illustrative of the present invention and should not be considered as limitative thereof in any manner.

Preparation A

A solution of p-methoxybenzylmagnesium chloride was prepared from 97.2 g of magnesium turnings and p-methoxybenzyl chloride (32.78 g) in 440 ml ether according to the procedure described in The Journal of the American Chemical Society, 76, 1886 (1954), except that no iodine was used to initiate the reaction. The above solution was decanted under nitrogen into a pressure-equilibrated addition funnel above a flask containing epichlorohydrin (30.5 g) in ether (150 ml), the excess magnesium being washed with ether to ensure complete transfer of the Grignard reagent. The solution of p-methoxybenzylmagnesium chloride was then added dropwise with stirring under gentle reflux to the epichlorohydrin over about 40 minutes, and stirring and reflux maintained for a further hour and the mixture allowed to stand overnight. A saturated solution of ammonium chloride was added with stirring until no solid remained, whereupon the ether layer was separated and the aqueous phase reextracted with ether. The combined extracts were washed with water, dried ($MgSO_4$), evaporated and the residue distilled in vacuo collecting the fraction of bp 140°–141° (0.3 mm Hg) to give 27.5 g of 1-chloro-4-(4-methoxyphenyl)-2-butanol as a colorless oil.

Similarly, proceeding as above, substituting the appropriately substituted benzyl chloride for p-methoxybenzyl chloride, there may be prepared, for example, the following compounds:
1-chloro-4-(4-chlorophenyl)-2-butanol,
1-chloro-4-(4-fluorophenyl)-2-butanol,
1-chloro-4-(4-methylphenyl)-2-butanol,
1-chloro-4-(4-tert-butylphenyl)-2-butanol,
1-chloro-4-(4-ethoxyphenyl)-2-butanol,
1-chloro-4-(4-tert-butoxyphenyl)-2-butanol,
1-chloro-4-(2,4-dichlorophenyl)-2-butanol.

Preparation B

A solution of sodium imidazole was prepared by the portionwise addition of sodium hydride (6.77 g of 50% dispersion in mineral oil) to imidazole (10.8 g) in dry dimethylformamide (80 ml). The resulting mixture was treated dropwise with stirring at 50° C. with 1-chloro-4-(4-methoxyphenyl)-2-butanol (27.5 g) and the mixture stirred overnight at 50° and for six hours at 90° C. The mixture was diluted with water (with stirring) to about 250 ml, hexane (50 ml) added whereupon the product started to precipitate. After the addition of water until no further turbidity resulted, the product was filtered off, washed well with cold water and hexane and dried in air. Recrystallization from ethyl acetate/hexane gave 1-[2-hydroxy-4-(4-methoxyphenyl)-n-butyl]imidazole (21.2 g) as snow-white granules, mp 103°–105° C.

Similarly, proceeding as above, substituting the appropriate chlorohydrin for 1-chloro-4-(4-methoxyphenyl)-2-butanol, there may be prepared, for example, the following compounds:
1-[2-hydroxy-4-(4-chlorophenyl)-n-butyl]imidazole,
1-[2-hydroxy-4-(4-fluorophenyl)-n-butyl]imidazole,
1-[2-hydroxy-4-(4-methylphenyl)-n-butyl]imidazole,
1-[2-hydroxy-4-(4-tert-butylphenyl)-n-butyl]imidazole,
1-[2-hydroxy-4-(4-ethoxyphenyl)-n-butyl]imidazole,
1-[2-hydroxy-4-(4-tert-butoxyphenyl)-n-butyl]imidazole, 1-[2-hydroxy-4-(2,4-dichlorophenyl)-n-butyl]imidazole.

Preparation C

1-[2-Hydroxy-4-(4-methoxyphenyl)-n-butyl]imidazole (2.0 g) was treated with thionyl chloride (10 ml) and the solution stirred for one hour at 60° C. The solvent was then evaporated under reduced pressure and the residue crystallized from ethyl acetate/ether, filtered, washed with ethyl acetate and dried in air to give 1-[2-chloro-4-(4-methoxyphenyl)-n-butyl]imidazole hydrochloride.

Similarly, preoceeding as above, substituting the appropriate alcohol of formula (II) for 1-[2-hydroxy-4-(4-methoxyphenyl)-n-butyl]imidazole, there may be prepared, for example, the hydrochloride salts of the following compounds:
1-[2-chloro-4-(4-chlorophenyl)-n-butyl]imidazole,
1-[2-chloro-4-(4-fluorophenyl)-n-butyl]imidazole,
1-[2-chloro-4-(4-methylphenyl)-n-butyl]imidazole,
1-[2-chloro-4-(4-tert-butylphenyl)-n-butyl]imidazole,
1-[2-chloro-4-(4-ethoxyphenyl)-n-butyl]imidazole,
1-[2-chloro-4-(4-tert-butoxyphenyl)-n-butyl]imidazole,
1-[2-chloro-4-(2,4-dichlorophenyl)-n-butyl]imidazole.

Preparation D

1-[2-Hydroxy-4-(4-chlorophenyl)-n-butyl]imidazole (2.0 g) in thionyl chloride (10 ml) was warmed for one hour at 65° C. The excess thionyl chloride was removed in vacuo and the residue dissolved in dichloromethane (75 ml) and shaken with excess aqueous potassium carbonate. The organic layer was washed with water, dried (MgSO₄), evaporated and the residue evacuated to remove all traces of dichloromethane to afford 1-[2-chloro-4-(4-chlorophenyl)-n-butyl]imidazole.

Similarly, proceeding as above, substituting the appropriate alcohol of formula (II) for 1-[2-hydroxy-4-(4-chlorophenyl)-n-butyl]imidazole, there may be prepared, for example, the following compounds:
1-[2-chloro-4-(4-methoxyphenyl)-n-butyl]imidazole,
1-[2-chloro-4-(4-fluorophenyl)-n-butyl]imidazole,
1-[2-chloro-4-(4-methylphenyl)-n-butyl]imidazole,
1-[2-chloro-4-(4-tert-butylphenyl)-n-butyl]imidazole,
1-[2-chloro-4-(4-ethoxyphenyl)-n-butyl]imidazole,
1-[2-chloro-4-(4-tert-butoxyphenyl)-n-butyl]imidazole,
1-[2-chloro-4-(2,4-dichlorophenyl)-n-butyl]imidazole.

EXAMPLE 1

A mixture of 1-[2-chloro-4-(4-methoxyphenyl)-n-butyl]imidazole hydrochloride (prepared from 2.00 g. of alcohol as in Preparation C), 2-chlorothiophenol (2.80 g) and anhydrous potassium carbonate (2.70 g) in acetone (50 ml) was heated under reflux with stirring overnight. After removal of the solvent under reduced pressure, ether (150 ml) was added and the extract washed with water (2×30 ml) and dried (MgSO₄) and the solvent removed to afford 1-[2-(2-chlorophenylthio)-4-(4-methoxyphenyl)-n-butyl]imidazole. Dropwise addition of 70% nitric acid (d-1.42) to an ethereal solution of this material until precipitation was complete gave the nitrate salt of 1-[2-(2-chlorophenylthio)-4-(4-methoxyphenyl)-n-butyl]imidazole, recrystallized from acetone/ethyl acetate as colorless microcrystals (3.10 g), mp 131.5°–133.5° C.

EXAMPLE 2

1-[2-Chloro-4-(4-chlorophenyl)-n-butyl]imidazole (prepared from 2.0 g of alcohol as in Preparation D) was treated with 2-methoxythiophenol (1.68 g) and anhydrous potassium carbonate (1.60 g) in acetone using the procedure of Example 1 to afford 1-[2-(2-methoxyphenylthio)-4-(4-chlorophenyl)-n-butyl]imidazole which was converted to its nitrate salt and recrystallized from ethyl acetate to give 3.10 g of microcrystals, mp 105°–106.5° C.

EXAMPLE 3

A stirred room temperature solution of 1-[2-hydroxy-4-(4-methoxyphenyl)-n-butyl]imidazole (2.00 g) in dry tetrahydrofuran (30 ml) was treated successively with 2-chlorophenol (1.56 g), diethyl azodicarboxylate (2.10 g) and triphenylphosphine (3.15 g). After stirring overnight, the solution was evaporated to dryness, the residue dissolved in ether (125 ml) and the ethereal solution treated dropwise with 70% nitric acid (d=1.42) until precipitation was complete. The precipitate was collected and neutralized by stirring in 100 ml of ether with excess aqueous potassium carbonate until no solid remained. The ethereal layer was separated, dried (MgSO₄), evaporated and the residue chromatographed on silica gel eluting with acetone (2% to 30%) in dichloromethane to remove an impurity. The pure product was again converted to the nitrate salt and the resulting precipitate of 1-[2-(2-chlorophenoxy)-4-(4-methoxyphenyl)-n-butyl]imidazole nitrate was filtered off, washed with a little ethyl acetate and recrystallized from ethyl acetate, m.p. 94.5°–96.5° C. (snow-white microcrystals).

EXAMPLE 4

Following the procedures in Preparation A, B and C, and Example 1 or Preparation A, B and D and Example 2, using equivalent amounts of the appropriate starting materials, there may be obtained the following compounds. Where indicated, the compounds may be further characterized by conversion to the indicated acid addition salt.
1-[2-(2-methoxyphenylthio)-4-(4-fluorophenyl)-n-butyl]imidazole-nitrate salt, mp 86.5°–87.5° C.,
1-[2-(2,4,6-trimethoxyphenylthio)-4-(4-fluorophenyl)-n-butyl]imidazole,
1-[2-(2-methoxyphenylthio)-4-(4-methoxyphenyl)-n-butyl]imidazole-nitrate salt, mp 130°–132.5° C.,
1-[2-(2,4,6-trichlorophenylthio)-4-(4-methoxyphenyl)-n-butyl]imidazole-nitrate salt, mp 178.5°–181.5° C.,
1-[2-(2,4,5-trichlorophenylthio)-4-(4-methoxyphenyl)-n-butyl]imidazole-nitrate salt, mp 163.5°–164° C.,
1-[2-(2,5-dichlorophenylthio)-4-(4-methoxyphenyl)-n-butyl]imidazole-nitrate salt, mp 146.5°–147° C.,
1-[2-(2-bromophenylthio)-4-(4-methoxyphenyl)-n-butyl]imidazole,
1-[2-(2-fluorophenylthio)-4-(4-methoxyphenyl)-n-butyl]imidazole,
1-[2-(2-methylphenylthio)-4-(4-methoxyphenyl)-n-butyl]imidazole,
1-[2-(2-tert-butylphenylthio)-4-(4-methoxyphenyl)-n-butyl]imidazole,
1-[2-(2,4,6-trimethoxyphenylthio)-4-(4-chlorophenyl)-n-butyl]imidazole,
1-[2-(2-methoxyphenylthio)-4-(4-methylphenyl)-n-butyl]imidazole,
1-[2-(2-methoxyphenylthio)-4-(4-tert.-butylphenyl)-n-butyl]imidazole,
1-[2-(2-chlorophenylthio)-4-(4-ethoxyphenyl)-n-butyl]imidazole,
1-[2-(2-methoxyphenylthio)-4-(4-tert.-butoxyphenyl)-n-butyl]imidazole, 1-[2-(2-methoxyphenylthio)-4-(2,4-dichlorophenyl)-n-butyl]imidazole,
1-[2-(2,4,6-trimethoxyphenylthio)-4-(2,4-dichlorophenyl)-n-butyl]imidazole,
1-[2-(2-ethoxyphenylthio)-4-(4-chlorophenyl)-n-butyl]imidazole,
1-[2-(2-n-propoxyphenylthio)-4-(4-chlorophenyl)-n-butyl]imidazole,
1-[2-(2-isopropoxyphenylthio)-4-(4-chlorophenyl)-n-butyl]imidazole,
1-[2-(2-chloro-4-methoxyphenylthio)-4-(4-chlorophenyl)-n-butyl]imidazole,
1-[2-(2-chloro-5-methoxyphenylthio)-4-(4-chlorophenyl)-n-butyl]imidazole,
1-[2-(2-methoxy-5-chlorophenylthio)-4-(4-chlorophenyl)-n-butyl]imidazole,
1-[2-(2-methoxy-4-chlorophenylthio)-4-(4-chlorophenyl)-n-butyl]imidazole,
1-[2-(2-methoxy-3-chlorophenylthio)-4-(4-chlorophenyl)-n-butyl]imidazole,
1-[2-(3-methoxyphenylthio)-4-(4-chlorophenyl)-n-butyl]imidazole,
1-[2-(4-methoxyphenylthio)-4-(4-chlorophenyl)-n-butyl]imidazole,
1-[2-(2,3-dimethoxyphenylthio)-4-(4-chlorophenyl)-n-butyl]imidazole,
1-[2-(2,4-dimethoxyphenylthio)-4-(4-chlorophenyl)-n-butyl]imidazole,
1-[2-(2,5-dimethoxyphenylthio)-4-(4-chlorophenyl)-n-butyl]imidazole,
1-[2-(2,6-dimethoxyphenylthio)-4-(4-chlorophenyl)-n-butyl]imidazole,
1-[2-(3-chlorophenylthio)-4-(4-methoxyphenyl)-n-butyl]imidazole,
1-[2-(4-chlorophenylthio)-4-(4-methoxyphenyl)-n-butyl]imidazole,
1-[2-(2,4-dichlorophenylthio)-4-(4-methoxyphenyl)-n-butyl]imidazole,
1-[2-(2,6-dichlorophenylthio)-4-(4-methoxyphenyl)-n-butyl]imidazole,
1-[2-(4-methylphenylthio)-4-(4-methoxyphenyl)-n-butyl]imidazole,
1-[2-(2,4-dimethylphenylthio)-4-(4-methoxyphenyl)-n-butyl]imidazole,
1-[2-(2,5-dimethylphenylthio)-4-(4-methoxyphenyl)-n-butyl]imidazole,
1-[2-(2,6-dimethylphenylthio)-4-(4-methoxyphenyl)-n-butyl]imidazole,
1-[2-(2,4,6-trimethylphenylthio)-4-(4-methoxyphenyl)-n-butyl]imidazole,
1-[2-(2-ethylphenylthio)-4-(4-methoxyphenyl)-n-butyl]imidazole,
1-[2-(2-isopropylphenylthio)-4-(4-methoxyphenyl)-n-butyl]imidazole,
1-[2-(4-methoxyphenylthio)-4-(4-methoxyphenyl)-n-butyl]imidazole,
1-[2-(2-ethylphenylthio)-4-(4-methoxyphenyl)-n-butyl]imidazole,
1-[2-(2-methoxyphenylthio)-4-(4-methylphenyl)-n-butyl]imidazole,
1-[2-(2-methoxy-5-chlorophenylthio)-4-(4-methylphenyl)-n-butyl]imidazole,
1-[2-(2-chloro-5-methoxyphenylthio)-4-(4-methylphenyl)-n-butyl]imidazole,
1-[2-(2-chloro-4-methoxyphenylthio)-4-(4-methylphenyl)-n-butyl]imidazole,
1-[2-(2-methoxy-4-chlorophenylthio)-4-(4-methylphenyl)-n-butyl]imidazole,
1-[2-(2-chlorophenylthio)-4-(4-tert.-butoxyphenyl)-n-butyl]imidazole,
1-[2-(2,4-dichlorophenylthio)-4-(4-tert.-butoxyphenyl)-n-butyl]imidazole,
1-[2-(2,5-dichlorophenylthio)-4-(4-tert.-butoxyphenyl)-n-butyl]imidazole,
1-[2-(2,6-dichlorophenylthio)-4-(4-tert.-butoxyphenyl)-n-butyl]imidazole,
1-[2-(2-methylphenylthio)-4-(4-tert.-butoxyphenyl)-n-butyl]imidazole,
1-[2-(2,6-dimethylphenylthio)-4-(4-tert.-butoxyphenyl)-n-butyl]imidazole, and
1-[2-(2,5-dimethylphenylthio)-4-(4-tert.-butoxyphenyl)-n-butyl]imidazole.

EXAMPLE 5

Following the procedures of Preparation A and B and Example 3, using equivalent amounts of the appropriate starting materials, these may be obtained the following compounds. Where indicated, the compounds may be further characterized by conversion to the indicated acid addition salt.

1-[2-(2-methoxyphenoxy)-4-(4-chlorophenyl)-n-butyl]imidazole,
1-[2-(2,4,6-trimethoxyphenoxy)-4-(4-fluorophenyl)-n-butyl]-imidazole,
1-[2-(2-methoxyphenoxy)-4-(4-methoxyphenyl)-n-butyl]-imidazole,
1-[2-(2,4,6-trichlorophenoxy)-4-(4-methoxyphenyl)-n-butyl]imidazole,
1-[2-(2,4,5-trichlorophenoxy)-4-(4-methoxyphenyl)-n-butyl]imidazole,
1-[2-(2,5-dichlorophenoxy)-4-(4-methoxyphenyl)-n-butyl]imidazole,
1-[2-(2-bromophenoxy)-4-(4-methoxyphenyl)-n-butyl]-imidazole
1-[2-(2-fluorophenoxy)-4-(4-methoxyphenyl)-n-butyl]imidazole,
1-[2-(2-methylphenoxy)-4-(4-methoxyphenyl)-n-butyl]imidazole,
1-[2-(2-tert-butylphenoxy)-4-(4-methoxyphenyl)-n-butyl]imidazole,
1-[2-(2,4,6-trimethoxyphenoxy)-4-(4-chlorophenyl)-n-butyl]imidazole,
1-[2-(2-methoxyphenoxy)-4-(4-methylphenyl)-n-butyl]-imidazole,
1-[2-(2-methoxyphenoxy)-4-(4-tert.-butylphenyl)-n-butyl]imidazole,
1-[2-(2-chlorophenoxy)-4-(4-ethoxyphenyl)-n-butyl]-imidazole,
1-[2-(2-methoxyphenoxy)-4-(4-tert.-butoxyphenyl)-n-butyl]imidazole,
1-[2-(2-methoxyphenyl)-4-(2,4-dichlorophenyl)-n-butyl]imidazole
1-[2-(2,4,6-trimethoxyphenoxy)-4-(2,4-dichlorophenyl)-n-butyl]imidazole,
1-[2-(2-ethoxyphenoxy)-4-(4-chlorophenyl)-n-butyl]-imidazole,
1-[2-(2-n-propoxyphenoxy)-4-(4-chlorophenyl)-n-butyl]imidazole,
1-[2-(2-isopropoxyphenoxy)-4-(4-chlorophenyl)-n-butyl]imidazole,
1-[2-(2-chloro-4-methoxyphenoxy)-4-(4-chlorophenyl)-n-butyl]imidazole,
1-[2-(2-chloro-5-methoxyphenoxy)-4-(4-chlorophenyl)-n-butyl]imidazole,
1-[2-(2-methoxy-5-chlorophenoxy)-4-(4-chlorophenyl)-n-butyl]imidazole, 1-[2-(2-methoxy-4-chlorophenoxy)-4-(4-chlorophenyl)-n-butyl]imidazole,
1-[2-(2-methoxy-3-chlorophenoxy)-4-(4-chlorophenyl)-n-butyl]imidazole,
1-[2-(3-methoxyphenoxy)-4-(4-chlorophenyl)-n-butyl]imidazole,
1-[2-(4-methoxyphenoxy)-4-(4-chlorophenyl-n-butyl]imidazole,
1-[2-(2,3-dimethoxyphenoxy)-4-(4-chlorophenyl)-n-butyl]imidazole,
1-[2-(2,4-dimethoxyphenoxy)-4-(4-chlorophenyl)-n-butyl]imidazole,
1-[2-(2,5-dimethoxyphenoxyl)-4-(4-chlorophenyl)-n-butyl]imidazole,
1-[2-(2,6-dimethoxyphenoxy)-4-(4-chlorophenyl)-n-butyl]imidazole,
1-[2-(3-chlorophenoxy)-4-(4-methoxyphenyl)-n-butyl]imidazole,
1-[2-(4-chlorophenoxy)-4-(4-methoxyphenyl)-n-butyl]imidazole,
1-[2-(2,4-dichlorophenoxy)-4-(4-methoxyphenyl)-n-butyl]imidazole,
1-[2-(2,6-dichlorophenoxy)-4-(4-methoxyphenyl)-n-butyl]imidazole,
1-[2-(4-methylphenoxy)-4-(4-methoxyphenyl)-n-butyl]imidazole,
1-[2-(2,4-dimethylphenoxy)-4-(4-methoxyphenyl)-n-butyl]imidazole,
1-[2-(2,5-dimethylphenoxy)-4-(4-methoxyphenyl)-n-butyl]imidazole,
1-[2-(2,6-dimethylphenoxy)-4-(4-methoxyphenyl)-n-butyl]imidazole,
1-[2-(2,4,6-trimethylphenoxy)-4-(4-methoxyphenyl)-n-butyl]imidazole,
1-[2-(2-ethylphenoxy)-4-(4-methoxyphenyl)-n-butyl]imidazole,
1-[2-(2-isopropylphenoxy)-4-(4-methoxyphenyl)-n-butyl]imidazole,
1-[2-(4-methoxyphenoxy)-4-(4-methoxyphenyl)-n-butyl]imidazole,
1-[2-(2-ethylphenoxy)-4-(4-methoxyphenyl)-n-butyl]imidazole,
1-[2-(2-methoxyphenoxy)-4-(4-methylphenyl)-n-butyl]imidazole,
1-[2-(2-methoxy-5-chlorophenoxy)-4-(4-methylphenyl)-n-butyl]imidazole,
1-[2-(2-chloro-5-methoxyphenoxy)-4-(4-methylphenyl)-n-butyl]imidazole,
1-[2-(2-chloro-4-methoxyphenoxy)-4-(4-methylphenyl)-n-butyl]imidazole,
1-[2-(2-methoxy-4-chlorophenoxy)-4-(4-methylphenyl)-n-butyl]imidazole,
1-[2-(2-chlorophenoxy)-4-(4-tert.-butoxyphenyl)-n-butyl]imidazole,
1-[2-(2,4-dichlorophenoxy)-4-(4-tert.-butoxyphenyl)-n-butyl]imidazole,
1-[2-(2,5-dichlorophenoxy)-4-(4-tert.-butoxyphenyl)-n-butyl]imidazole,
1-[2-(2,6-dichlorophenoxy)-4-(4-tert.-butoxyphenyl)-n-butyl]imidazole,
1-[2-(2-methylphenoxy)-4-(4-tert.-butoxyphenyl)-n-butyl]imidazole,
1-[2-(2,6-dimethylphenoxy)-4-(4-tert.-butoxyphenyl)-n-butyl]imidazole, and
1-[2-(2,5-dimethylphenoxy)-4-(4-tert.-butoxyphenyl)-n-butyl]imidazole.

EXAMPLE 6

Nitric acid (70%; d=1.42) was added dropwise to a stirred solution of 2.0 g of 1-[2-(2-chlorophenylthio)-4-(4-methoxyphenyl)-n-butyl]imidazole in 30 ml of anhydrous ether until precipitation was complete. The product was filtered off, washed with ether, air dried, and recrystallized from ethyl acetate to yield 1-[2-(2-chlorophenylthio)-4-(4-methoxyphenyl)n-butyl]imidazole nitrate, mp 131.5°–133.5° C.

In similar manner, all compounds of Formula (I) in base form can be converted to their antimicrobial acid addition salts by treatment with the appropriate acid, for example, hydrochloric acid, hydrobromic acid, sulfuric acid, nitric acid, phosphoric acid, acetic acid, propionic acid, glycolic acid, lactic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid or p-toluenesulfonic acid.

EXAMPLE 7

1-[2-(2-chlorophenylthio)-4-(4-methoxyphenyl)-n-butyl]imidazole nitrate (2.0 g) in 100 ml of dichloromethane was shaken with excess dilute potassium carbonate solution until the salt was completely dissolved. The organic layer was then separated, washed twice with water, dried over magnesium sulfate and evaporated to yield 1-[2-(2-chlorophenylthio)-4-(4-methoxyphenyl)-n-butyl]imidazole as an oil.

In similar manner, the antimicrobial acid addition salts of all compounds of Formula (I) can be converted to the corresponding compounds in base form.

EXAMPLE 8

The following illustrates the preparation of representative pharmaceutical formulations which may be used for controlling fungi, bacteria and protozoa, utilizing an active compound of Formula (I) such as the nitrate salt of 1-[2-(2-chlorophenylthio)-4-(4-methoxyphenyl)-n-butyl]imidazole.

| A. | Topical Formulation | grams |
| --- | --- | --- |
| | Active compound | 0.2–2 |
| | Span 60 | 2 |
| | Tween 60 | 2 |
| | Mineral oil | 5 |
| | Petrolatum | 10 |
| | Methyl paraben | 0.15 |
| | Propyl paraben | 0.05 |
| | BHA (butylated hydroxy anisole) | 0.01 |
| | Water qs | 100 |

All of the above ingredients, except water, are combined and heated at 60° C. with stirring. A sufficient quantity of water at 60° C. is then added with vigorous stirring to provide 100 g of the cream formulation which is then cooled to room temperature.

| B | I.V. Formulation | |
| --- | --- | --- |
| | Active compound | 0.5 g. |
| | Propylene glycol | 20 g. |
| | Polyethylene glycol 400 | 20 g. |
| | Tween 80 | 1 g. |
| | 0.9 Saline solution qs | 100 ml. |

The active compound is dissolved in propylene glycol, polyethylene glycol 400 and Tween 80. A sufficient quantity of 0.9% saline solution is then added with stirring to provide 100 ml of the I.V. solution which is filtered through a 0.2 micron membrane filter and packaged under sterile conditions.

| C. | Oral Formulation | parts by weight |
|---|---|---|
| | Active compound | 200 |
| | Magnesium stearate | 3 |
| | Starch | 30 |
| | Lactose | 116 |
| | PVP (polyvinylpyrrolidone) | 3 |

The above ingredients are combined and granulated using methanol as the solvent. The formulation is then dried and formed into tablets (containing 200 mg of active compound) with an appropriate tabletting machine.

EXAMPLE 9

The following example illustrates acute oral toxicity of representative compounds.

Protocol: The test compound is suspended in an aqueous carboxymethyl cellulose suspending vehicle. Concentrations are adjusted so that doses can be given in volumes of 10 ml./kg. body weight. Groups of mice comprising six Swiss-Webster male mice in each group are used. A single oral dose, by stomach tube, of a final dosage of test compound is administered to the mice in each group. Each group receives a different dosage, one group serving as a control. After administration the mice are observed for a three week period.

Using the above protocol, the acute oral $LD_{50}$ value of the test compounds are as follows:

1-[2-(2-methoxyphenylthio)-4-(4-chlorophenyl)-n-butyl]imidazole nitrate->2000 mg./kg.

1-[2-(2-chlorophenylthio)-4-(4-methoxyphenyl)-n-butyl]imidazole nitrate->2000 mg./kg.

I claim as my invention:

1. A compound of the formula $$R^1-CH-CH_2-N \overset{\frown}{\underset{\smile}{\phantom{xx}}} N \qquad (I)$$
$$\phantom{R^1-C}|$$
$$\phantom{R^1-}X-R^2$$

wherein $R^1$ is phenethyl and $R^2$ is phenyl, each of said phenethyl or phenyl independently being unsubstituted or substituted in the phenyl ring by from 1 to 3 substituents selected from the group consisting of halo, lower alkyl and lower alkoxy with the proviso that at least one of $R^1$ and $R^2$ be substituted by lower alkoxy; X is oxygen in sulfur and the antimicrobial acid addition salts thereof.

2. The compound of claim 1 wherein X is sulfur.

3. The compound of claim 2 wherein $R^1$ has a 4-halo or 4-lower alkyl substituent and $R^2$ has a lower alkoxy substituent.

4. The compound of claim 3 wherein $R^1$ has a 4-chloro or 4-methyl substituent and $R^2$ has a lower alkoxy in the 2-position.

5. The compound of claim 4 wherein $R^2$ is mono-substituted.

6. The compound of claim 5 wherein $R^2$ has a 2-methoxy substituent.

7. The compound of claim 6 which is 1-[2-(2-methoxyphenylthio)-4-(4-chlorophenyl)-n-butyl]imidazole and the antimicrobial acid addition salts thereof.

8. The compound of claim 2 wherein $R^1$ has a 4-lower alkoxy substituent and $R^2$ has a 2-halo, 2-lower alkyl or 2-lower alkoxy substituent.

9. The compound of claim 8 wherein $R^1$ has a 4-methoxy substituent and $R^2$ has a 2-chloro, 2-methyl or 2-methoxy substituent.

10. The compound of claim 9 which is 1-[2-(2-methoxyphenylthio)-4-(4-methoxyphenyl)-n-butyl]imidazole and the antimicrobial acid addition salts thereof.

11. The compound of claim 9 which is 1-[2-(2-chlorophenylthio)-4-(4-methoxyphenyl)-n-butyl]imidazole and the antimicrobial acid addition salts thereof.

12. The compound of claim 9 which is 1-[2-(2,4,6-trichlorophenylthio)-4-(4-methoxyphenyl)-n-butyl]imidazole and the antimicrobial acid addition salts thereof.

13. The compound of claim 9 which is 1-[2-(2,4,5-trichlorophenylthio)-4-(4-methoxyphenyl)-n-butyl]imidazole and the antimicrobial acid addition salts thereof.

14. The compound of claim 9 which is 1-[2-(2,5-dichlorophenylthio)-4-(4-methoxyphenyl)-n-butyl]imidazole and the antimicrobial acid addition salts thereof.

15. A composition useful for inhibiting the growth of fungi, bacteria or protozoa which comprises an effective amount of a compound of the formula $$R^1-CH-CH_2-N \overset{\frown}{\underset{\smile}{\phantom{xx}}} N \qquad (I)$$
$$\phantom{R^1-C}|$$
$$\phantom{R^1-}X-R^2$$

wherein $R^1$ is phenethyl and $R^2$ is phenyl, each of said phenethyl or phenyl independently being unsubstituted or substituted in the phenyl ring by from 1 to 3 substituents selected from the group consisting of halo, lower alkyl and lower alkoxy with the proviso that at least one of $R^1$ and $R^2$ is substituted by lower alkoxy; X is oxygen or sulfur and the antimicrobial acid addition salts thereof; in admixture with a suitable carrier.

16. The composition of claim 15 suitable for pharmaceutical use wherein the carrier is a pharmaceutically acceptable, non-toxic carrier.

17. The composition of claim 16 for topical administration wherein the compound of Formula I is present as between about 0.1 and 10.0 weight percent of the composition.

18. A method of inhibiting the growth of fungi, bacteria or protozoa which comprises applying to a host object containing, or subject to attack by, fungi, bacteria or protozoa an effective amount of a compound of the formula $$R^1-CH-CH_2-N \overset{\frown}{\underset{\smile}{\phantom{xx}}} N \qquad (I)$$
$$\phantom{R^1-C}|$$
$$\phantom{R^1-}X-R^2$$

wherein $R^1$ is phenethyl and $R^2$ is phenyl, each of said phenethyl or phenyl independently being unsubstituted or substituted in the phenyl ring by from 1 to 3 substituents selected from the group consisting of halo, lower alkyl and lower alkoxy with the proviso that at least one of $R^1$ and $R^2$ be substituted by lower alkoxy; X is oxygen or sulfur or an antimicrobial acid addition salt thereof; or a composition containing same as an active ingredient.

19. The method of claim 18 wherein the compound of Formula I is administered topically.

20. The method of claim 18 wherein the compound of Formula I is administered parenterally.

* * * * *